(12) United States Patent
Fujii et al.

(10) Patent No.: US 10,098,592 B2
(45) Date of Patent: Oct. 16, 2018

(54) BLOOD FLOW IMAGE DIAGNOSING DEVICE AND METHOD

(71) Applicant: SOFTCARE CO., LTD., Fukuoka (JP)

(72) Inventors: Hitoshi Fujii, Fukuoka (JP); Kenji Okamoto, Fukuoka (JP); Noriyoshi Takahashi, Fukuoka (JP)

(73) Assignee: SOFTCARE CO., LTD., Fukuoka (JP)

( * ) Notice: Subject to any disclaimer, the term of this patent is extended or adjusted under 35 U.S.C. 154(b) by 380 days.

(21) Appl. No.: 14/391,539

(22) PCT Filed: Apr. 17, 2014

(86) PCT No.: PCT/JP2014/060909
§ 371 (c)(1),
(2) Date: Oct. 9, 2014

(87) PCT Pub. No.: WO2014/175154
PCT Pub. Date: Oct. 30, 2014

(65) Prior Publication Data
US 2016/0278718 A1    Sep. 29, 2016

(30) Foreign Application Priority Data

Apr. 23, 2013  (JP) ................................ 2013-090562

(51) Int. Cl.
*A61B 5/00* (2006.01)
*G06T 7/00* (2017.01)
(Continued)

(52) U.S. Cl.
CPC .......... *A61B 5/7282* (2013.01); *A61B 3/0025* (2013.01); *A61B 3/1233* (2013.01);
(Continued)

(58) Field of Classification Search
CPC .... A61B 5/00; A61B 3/00; G06T 7/00; G06T 5/00; G06T 2207/00
See application file for complete search history.

(56) References Cited

U.S. PATENT DOCUMENTS 5,725,480 A  * 3/1998  Oosta .................. A61B 5/0059
                                                     600/310
2004/0004695 A1 * 1/2004  Sugino ................. A61B 3/145
                                                     351/206

(Continued)

FOREIGN PATENT DOCUMENTS

EP    2 430 973 A1   3/2012
JP    H05-28134 B2   5/1989
(Continued)

OTHER PUBLICATIONS

Tsang, Alexander C., et al. "Brightness alters Heidelberg retinal flowmeter measurements in an in vitro model." Investigative ophthalmology & visual science 40.3 (1999): 795-799.*

(Continued)

*Primary Examiner* — Katherine Fernandez
*Assistant Examiner* — Sean D Mattson
(74) *Attorney, Agent, or Firm* — McGlew and Tuttle, P.C.

(57) ABSTRACT

A blood flow image diagnosing device of the present invention includes a laser light irradiation system for applying laser light to an observation region of a biotissue having blood cells; a light receiving section having a plurality of pixels and adapted to detect reflection light from the observation region of the biotissue; an image capturing section for successively capturing a plurality of images on the basis of a signal from the light receiving section; an image storage section for storing the plurality of images; a computation section for computing the speed of blood flow within the biotissue from time course changes of output signals of the pixels throughout the stored images; and a display section (Continued)

SCHEMATIC OVERALL CONFIGURATION for displaying a two-dimensional distribution which is the result of the computation as a blood flow map. The computation section includes a pigment concentration correction section.

4 Claims, 8 Drawing Sheets

(51) Int. Cl.
    *A61B 3/00* (2006.01)
    *G06T 5/00* (2006.01)
    *A61B 3/12* (2006.01)
    *A61B 5/026* (2006.01)

(52) U.S. Cl.
    CPC .......... *A61B 3/1241* (2013.01); *A61B 5/0261* (2013.01); *A61B 5/742* (2013.01); *G06T 5/00* (2013.01); *G06T 7/0012* (2013.01); *G06T 2207/10024* (2013.01); *G06T 2207/30088* (2013.01); *G06T 2207/30104* (2013.01)

(56) References Cited

U.S. PATENT DOCUMENTS

| | | | |
|---|---|---|---|
| 2008/0294017 A1* | 11/2008 | Gobeyn | A61B 3/113 600/301 |
| 2010/0056936 A1* | 3/2010 | Fujii | A61B 3/1241 600/504 |
| 2010/0141752 A1* | 6/2010 | Yamada | G01N 1/312 348/79 |
| 2011/0319775 A1 | 12/2011 | Fujii et al. | |
| 2013/0028484 A1 | 1/2013 | Wada et al. | |
| 2013/0096392 A1* | 4/2013 | Adams | A61B 5/0075 600/301 |

FOREIGN PATENT DOCUMENTS

| | | |
|---|---|---|
| JP | H04-242628 A | 8/1992 |
| JP | H05-28133 B2 | 4/1993 |
| JP | H08-112262 A | 5/1996 |
| JP | 2003-164431 A | 6/2003 |
| JP | 2003-180641 A | 7/2003 |
| JP | 2013-48889 A | 3/2013 |
| WO | 2008/069062 A1 | 6/2008 |
| WO | 2010/131550 A1 | 11/2010 |

OTHER PUBLICATIONS

"Blood Flow Imaging by Means of Laser Scattering": Fujii et al., CSE, Kyushu Institute of Technology: a review article presented by Medical Online, received Jul. 22, 2005, Accepted Aug. 11, 2005, pp. 266-271.

* cited by examiner

SCHEMATIC OVERALL CONFIGURATION

CONFIGURATION OF COMPUTATION SECTION

BLOOD FLOW IMAGE DIAGNOSING DEVICE AND METHOD

This application claims the benefit of PCT International Application Number PCT/JP2014/060909 filed on Apr. 17, 2014 and Japanese Application No. 2013-090562 filed on Apr. 23, 2013 in Japan, the disclosures of which are incorporated herein by reference.

TECHNICAL FIELD

The present invention relates to a blood flow image diagnosing device and a blood flow image diagnosing method which apply laser light to a biotissue having blood cells, and measure and image the speed of blood flow on the basis of a speckle signal reflected from the biotissue, and which suppress the influence of the concentration of pigment deposited in the biotissue on the measured value of the blood flow.

BACKGROUND ART

Heretofore, the present inventors have invented a blood flow speed measurement apparatus which applies laser light to a biotissue having blood cells such as the eyeground or the skin; leads a so-called speckle image (an image of random speckle pattern formed as a result of interference of reflection light from the blood cells) to an image sensor such as a solid state imaging device (CCD or CMOS); successively captures and stores a large number of speckle images at predetermined intervals; selects a predetermined number of images from the large number of stored images; calculates a value which reflects the speed of a time course change in the output of each pixel throughout the images; and calculates the speed of blood cells (blood flow speed) from the calculated value. In a blood flow speed measurement apparatus of such a type, since the value indicating the output changing speed of each pixel corresponds to the moving speed of blood cells, the blood flow distribution in the biotissue can be color-disposed on a monitor screen as a two-dimensional image (a blood flow map) on the basis of the calculated value indicating the output changing speed of each pixel. A blood flow map observed in actuality is composed of a series of blood flow maps (hereinafter also referred to as "original maps") calculated at a speed of about 30 frames per sec, and can be displayed as a motion video. Therefore, the invented apparatus has been put to practical use as an apparatus for observing the haemodynamics of the eyeground or skin (see Patent Documents 1 to 6).

Also, the present inventors have proposed a blood flow speed imaging apparatus (see Patent Document 7). In this apparatus, a series of blood flow maps obtained through blood flow measurement performed for several seconds are used, and a change in blood flow appearing periodically in synchronism with the heartbeat is analyzed in various regions within a field of observation view. A numerical value (i.e., the degree of distortion) is introduced so as to distinguish between a region having a sharp rising waveform attributable to the arterial blood flow and a region having a mildly rising and falling waveform attributable to the venous blood flow. Thus, the apparatus can display on the blood flow maps pulsations caused by the arterial blood flow and pulsations caused by the venous blood flow.

Moreover, the present inventors has proposed the following method. A new blood flow image diagnosing function is added to the conventional apparatus, and a function is added to a computation section so as to separate, from data of a plurality of blood flow maps over one or more heartbeats, a blood flow within a surface blood vessel within an observation region of a biotissue and the background blood flow therearound. These blood flows are displayed on the blood flow map on a display section in a distinguishable manner. Various variables which characterize the blood flow waveforms of the separated regions are defined, and these variables are compared for clinical diagnosis. In the following description, an apparatus having such a function added thereto will be referred to as a "blood flow image diagnosing device."

PRIOR ART DOCUMENTS

Patent Documents

Patent Document 1: Japanese Patent Publication (kokoku) No. H5-28133
Patent Document 2: Japanese Patent Publication (kokoku) No. H5-28134
Patent Document 3: Japanese Patent Application Laid-Open (kokai) No. H4-242628
Patent Document 4: Japanese Patent Application Laid-Open (kokai) No. H8-112262
Patent Document 5: Japanese Patent Application Laid-Open (kokai) No. 2003-164431
Patent Document 6: Japanese Patent Application Laid-Open (kokai) No. 2003-180641
Patent Document 7: WO 2008/69062.

SUMMARY OF THE INVENTION

Problems to be Solved by the Invention

It was found that in the case where the eyeground blood flow is measured using a conventional blood flow image diagnosing device, the measured value of blood flow changes depending on the light absorptivity of the tissue of the retina called "pigment epithelium." For example, in the case of caucasoids (white race), people hardly have that pigment unlike people of other races. Therefore, laser light used for measurement repeats scattering within the eye without attenuating. In contrast, in the case of colored races such as the yellow race and the negroid race, people have such pigment in a high concentration. Therefore, laser light is absorbed immediately without repeating scattering. This difference corresponds to the difference between a case where the interior surface of a camera is not treated to have a black matted surface and a case where the interior surface of a camera is treated to have a black matted surface. It is common knowledge for persons who design optical products that when such surface treatment is omitted, internal scattering light fogs a film or an image sensor, and adversely affects the quality of images (for example, contrast decreases).

In the blood flow imaging method developed by the present inventors, the distribution of blood flow speed is visualized using the reciprocal of the contrast of a speckle image which is formed on an image sensor as a result of interference of laser light scattered by the retina. However, when the contrast decreases as a result of the above-mentioned fog caused by light scattering within the eyeball, the blood flow value is displayed to be rather high (higher than the actual value). Since people of the white race are lower in pigment concentration than people of the colored races as described above, the degree of coherence decreases as a result of repetition of multiple scattering, and the contrast of a speckle image (interference fringes) lowers, whereby the blood flow value is displayed to be rather high. Under the assumption that the size of the eyeball does not differ greatly among the races, it is considered that the amount of blood circulating within the eyeball does not differ greatly among the races. Therefore, it is hard to accept the measurement result that caucasoid people are high in blood flow value than people of the colored races, and some correction is needed.

Intraocular blood flows which ophthalmologists consider important for diagnosis are the blood flows of the arterial and venous blood vessels on the retina, the tissue blood flow of the optic papilla, and the blood flow of the choroid. The arterial and venous blood vessels run through the surface layer of the retina, and, under this layer, the layer of visual cells, the layer of pigment epithelium, and the layer of choroid blood vessels are layered in this order toward the sclera which is the outmost layer. It is said that although the arterial and venous blood vessels of the retina extend through the optic papilla, the pigment epithelium is usually absent in the optic layer of the optic papilla other than the blood vessels. Accordingly, in the case of people of the colored races, the degree of influence of the pigment epithelium on scattering of laser light differ among regions, which leads to a complicated result in which the proportionality constant for equalizing the measured values of caucasoid people and those of colored people differs among regions. In other words, when the eyeground blood flow of a caucasoid person and that of a colored person are measured, equalizing the indicated values of the eyeground blood flows is not a simple task, and it becomes necessary to perform complicated processing of correcting the indicated values by applying different proportionality constants for different regions.

A similar problem arises when the skin blood flow is measured. The concentration of melanin greatly differs among the human races, and the darker the skin color, the lower the measured value of blood flow. Therefore, numerical comparison is difficult. Also, in the case where the color of the skin has changed due to lesion or a difference in color arises between an incision formed as a result of an operation and a region therearound, a numerical difference is produced as in the case of the above-described retina blood flow measurement. Therefore, in order to perform comparison in a standardized state, it is necessary to perform some correction in accordance with the pigment concentration.

An object of the present invention is to solve the problem of the conventional image analyzing apparatuses for eyeground blood flow and skin blood flow; i.e., the problem that the measured value of blood flow is displayed differently depending on the pigment concentration of a subject (object under measurement), and to provide means which allows the measured value of blood flow to be displayed by a standardized numerical value irrespective of the race of the subject and allows comparison of measured values among people of different races.

Means for Solving the Problems

A blood flow image diagnosing device of the present invention comprises a laser light irradiation system for applying laser light to an observation region of a biotissue having blood cells; a light receiving section having a plurality of pixels and adapted to detect reflection light from the observation region of the biotissue; an image capturing section for successively capturing a plurality of images on the basis of a signal from the light receiving section; an image storage section for storing the plurality of images; a computation section for computing the speed of blood flow within the biotissue from time course changes of output signals of the pixels through the plurality of stored images; and a display section for displaying a two-dimensional distribution which is the result of the computation as a blood flow map. The computation section includes a pigment concentration correction section for correcting the blood flow map obtained as a result of computation at the computation section in accordance with the pigment concentration of the observation region.

The pigment concentration correction section includes a laser reflectance computation section for detecting the pigment concentration of the observation region as a laser reflectance; and a correction coefficient creation section for creating a correction coefficient, which is used for correction of the blood flow map, on the basis of the laser reflectance from the laser reflectance computation section.

When a surface under measurement moves during capturing of images, the blood flow map shifts according. In view of this, the computation section includes a blood flow analysis section for performing tracking processing of calculating a shift amount of the blood flow map and superimposing it while correcting its movement amount; and a blood flow map creation section for correcting the blood flow map having undergone the tracking processing in accordance with the pigment concentration of the observation region, the correction being performed on the basis of the correction coefficient output from the pigment concentration correction section, wherein the laser reflectance computation section obtains the laser reflectance on the basis of a laser reflection intensity obtained from a laser reflection intensity map obtained by superimposing speckle images from which the blood flow map is synthesized, and a signal representing the intensity of laser light radiated from the laser light irradiation system.

The blood flow image diagnosing device further comprises a storage section for storing a relation between the laser reflectance and the blood flow value in the observation region, the relation being obtained in advance for a plurality of healthy persons, wherein the correction coefficient creation section creates the correction coefficient on the basis of the laser reflectance obtained for a newly measured blood flow map, and the relation between the laser reflectance and the blood flow value stored in the storage section. The laser reflectance is calculated on an observation region-by-observation region basis, and a different correction coefficient is created for each observation region. The blood flow of the biotissue is, for example, the eyeground blood flow or the skin blood flow. The correction performed in accordance with the pigment concentration of the skin tissue is composed of first-stage correction performed for a specific region where a relatively stable numerical value is obtained, and second-stage correction of multiplying a value obtained through the first-stage correction by correction coefficients determined for regions which differ from one another in terms of the pigment concentration and the scattering characteristic of the corneal layer of epidermis.

A blood flow image analysis method of the present invention uses a laser light irradiation system for applying laser light to an observation region of a biotissue having blood cells and a light receiving section having a plurality of pixels and adapted to detect reflection light from the observation region of the biotissue. The method comprises the steps of: successively capturing a plurality of images on the basis of a signal from the light receiving section and storing the plurality of images; computing the speed of blood flow within the biotissue from time course changes of output signals of the pixels throughout the stored images, and creating a blood flow map having a two-dimensional distribution; obtaining, in advance for a plurality of healthy persons, a relation between the laser reflectance and the blood flow value in the observation region, and storing the relation, the relation being used for creation of a correction coefficient used for correcting the blood flow map in accordance with the pigment concentration of the observation region; creating, at the time of new measurement, the correction coefficient on the basis of a newly obtained laser reflectance and the stored relation between the laser reflectance and the blood flow value; and displaying the blood flow map corrected on the basis of the correction coefficient.

Effect of the Invention

In the case of a conventional blood flow image diagnosing device, the blood flow measured value greatly differs between the white race and the colored race. However, according to the present invention, it becomes possible to suppress the influence of the concentration of pigment deposited in an object under measurement and allow standardized comparison of blood flow values among human races.

MODE FOR CARRYING OUT THE INVENTION

Figure 1A:
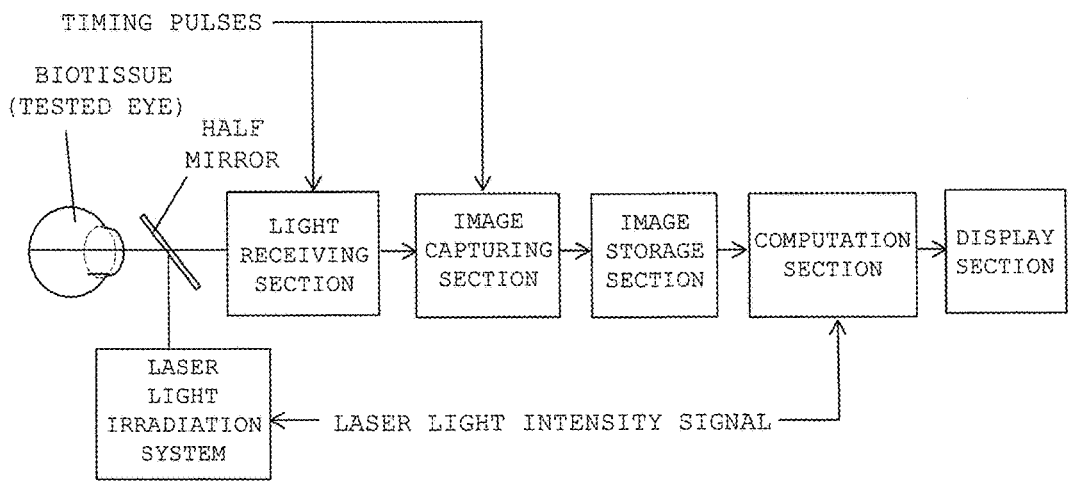
FIG. 1(A) is a schematic diagram showing the overall configuration of a blood flow image diagnosing device configured on the basis of the present invention.
Figure 1B:
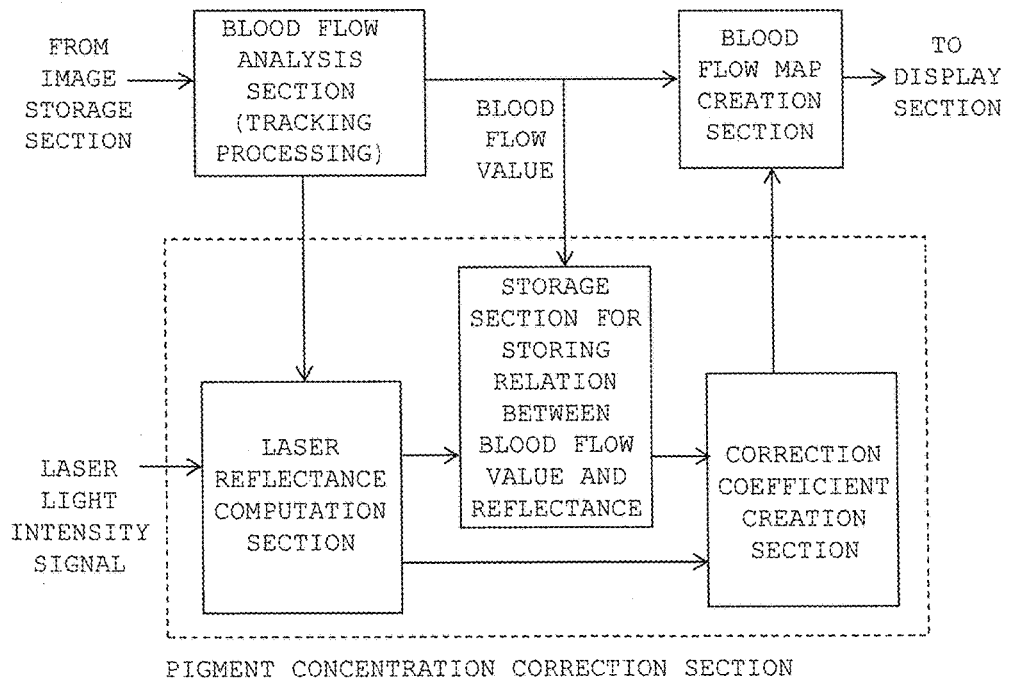
FIG. 1(B) is a diagram showing the configuration of a computation section which is the characteristic of the present invention.

The present invention will now be described by way of examples. FIG. 1(A) is a schematic diagram showing the overall configuration of a blood flow image diagnosing device configured on the basis of the present invention, and FIG. 1(B) is a diagram showing the configuration of a computation section which is the characteristic of the present invention. A laser light irradiation system applies laser light, through a half mirror, to a biotissue (e.g., the eyeground of an eye to be tested) having blood cells such as eyeground blood flow or skin blood flow. A light receiving section includes a CCD (solid state imaging device) having a large number of pixels on its light receiving surface, a light receiving lens which focuses laser reflection light on the CCD, an amplification circuit for amplifying the output of the CCD, etc. The CCD which is driven on the basis of timing pulses converts an image of the biotissue formed by the light receiving lens to an electric signal on the basis of the timing pulses. The CCD reads out signal charges in a frame storage mode, and amplifies and outputs them as an image signal.

Analog processing such as gain control is performed on the output image signal, and a resultant analog signal is converted to a digital signal. On the basis of this digital signal and the timing pulses, an image capturing section successively captures a plurality of images at predetermined intervals (e.g., intervals of 1/30 sec) equal to or greater than one heartbeat. An image storage section stores data of the captured images. A computation section computes the blood flow speed within the biotissue from the time course change of output signals of the pixels throughout the plurality of stored images. The characteristic feature of the present invention is correcting a blood flow map obtained as a result of the computation at the computation section in accordance with the pigment concentration of the observation region. As will be described in detail later, a laser light intensity signal is used for this correction. A display section displays a two-dimensional distribution of computation results as a blood flow map, and also displays numerical information which characterizes a blood flow waveform.

The above-described configuration of the blood flow image diagnosing device is identical to the conventional configuration disclosed in Patent Document 7, etc. except for the configuration of the computation section. The configuration of the computation section which is the feature of the present invention will be described with reference to FIG. 1(B). The present invention is characterized by providing a pigment concentration correction section which corrects the blood flow map obtained through computation in accordance with the pigment concentration of the observation region. Although the image storage section stores eyeground blood flow maps (original maps) obtained at a speed of, for example, 30 frames per sec, the quality of the images is not good enough as will be described in detail later. Therefore, tracking processing is performed in a blood flow analysis section. In the tracking processing, the amount of shift of each blood flow map is calculated, and the blood flow map is superimposed on other blood flow maps by correcting its movement amount. On the basis of the correction coefficient output from the pigment concentration correction section, a blood flow map creation section corrects the blood flow map having undergone the tracking processing in accordance with the pigment concentration of the observation region. The corrected blood flow map is displayed.

Since the reflectance (or absorptivity) of laser light differs among the human races, the pigment concentration is detected as a laser reflectance (reflection intensity/incident intensity). For such a purpose, a laser reflectance computation section obtains the laser reflectance of the observation region on the basis of a signal representing the intensity of the applied laser light and the intensity of a signal reflected from each location within the observation region and detected by the light receiving section. In the exemplified method, the intensity of the detected signal is obtained from a laser reflection intensity map which is obtained by superimposing speckle images from which a blood flow map is synthesized. The relation between the laser reflectance and the blood flow value in the observation region is obtained for a large number of healthy persons, and is stored in the apparatus (the storage section).

The correction coefficient creation section creates a correction coefficient for the blood flow value on the basis of the laser reflectance obtained for a newly measured blood flow map and the relation between the laser reflectance and the blood flow value stored in the storage section.

Figure 2:
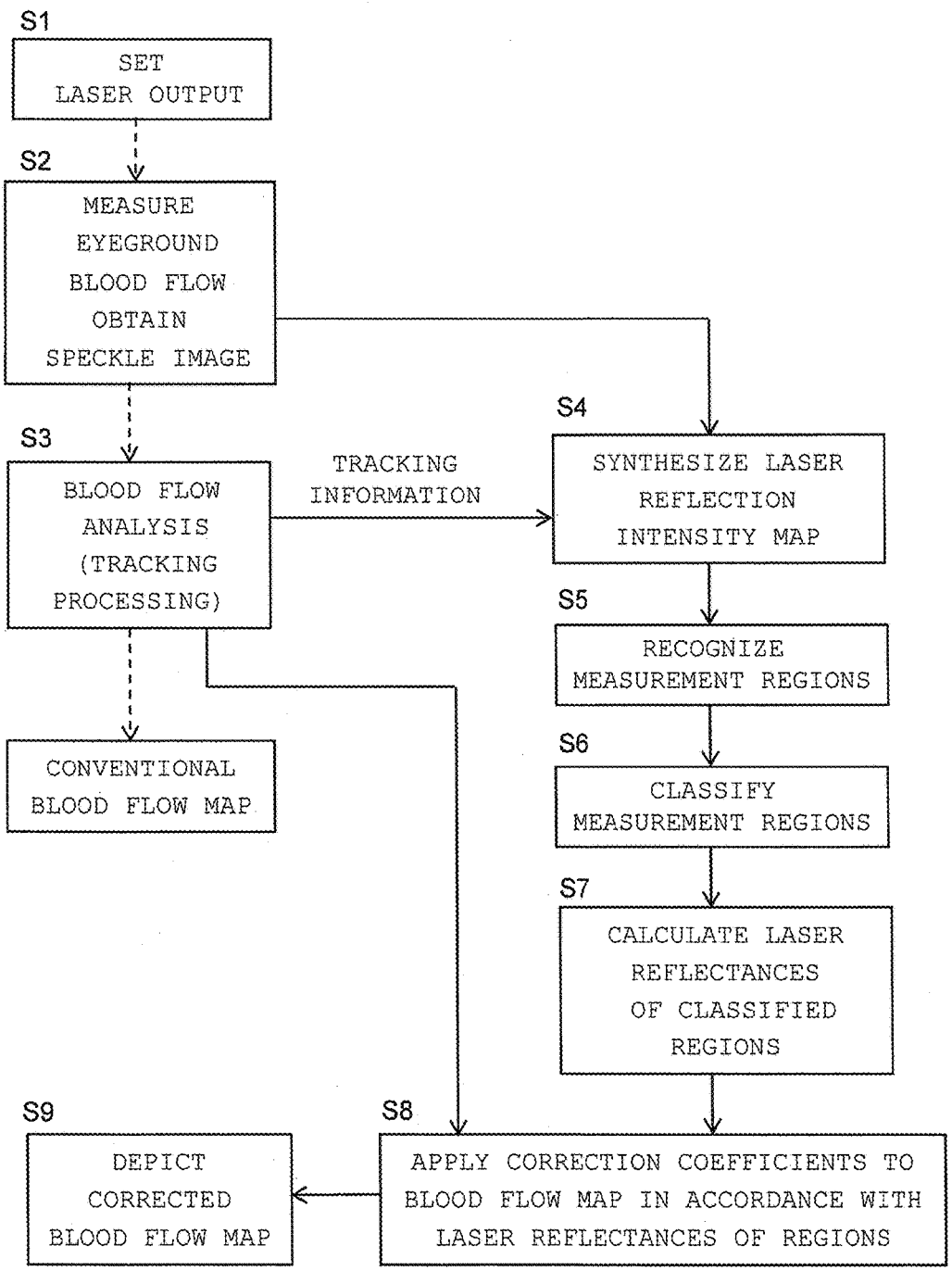
FIG. 2 is a flowchart showing operation of blood flow image diagnosis when applied to measurement of eyeground blood flow.

Next, operation of a first embodiment in which the blood flow image diagnosing device shown in FIGS. 1(A) and 1(B) is applied to measurement of the eyeground blood flow will be described with reference to FIG. 2. FIG. 2 is a flowchart showing operation of the blood flow image diagnosis when applied to measurement of the eyeground blood flow. In step S1 shown in FIG. 2, the output of a laser is set, and laser light is radiated. In step S2, the eyeground blood flow is measured by the blood flow image diagnosing device. When the surface of an organism is irradiated with laser light, scattering light rays interfere with one another and form a random speckle pattern. In general, this pattern is called "laser speckle." This speckle image is obtained.

Figure 3:
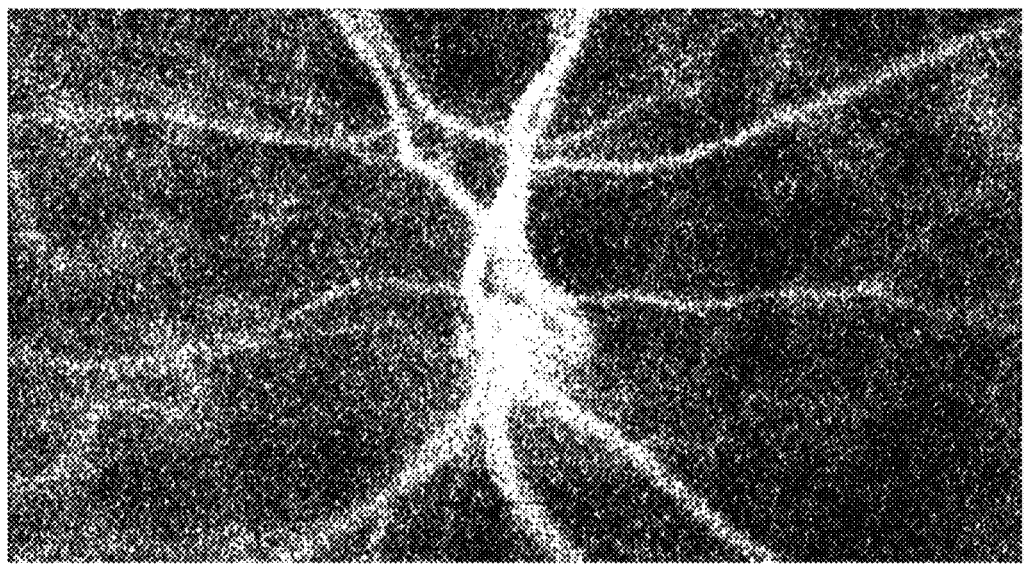
FIG. 3 is an image showing a display example in which eyeground blood flow maps (original maps) obtained at a speed of 30 frames per sec (an example for the case where the subject is the yellow race).

FIG. 3 is an image showing a display example in which eyeground blood flow maps (original maps) obtained at a speed of 30 frames per sec (an example for the case where the subject is the yellow race). The eyeground blood flow maps are stored in the image storage section shown in FIG. 1(A). As shown in FIG. 3, the blood flow maps are usually displayed as a motion video (30 fames per sec). However, the image quality is not high enough because the degree of graininess is large. Therefore, tracking processing is performed in step S3 of FIG. 2. In the tracking processing, each blood flow map is analyzed, the amount of shift of the map is calculated, and the blood flow map is superimposed on other blood flow maps by correcting its movement amount. When the surface under measurement moves during capturing of an image, the blood flow map shifts accordingly. The computation section has a function of performing so-called tracking processing of calculating the shift amount of each map and superimposing it while correcting the movement amount.

Figure 4:
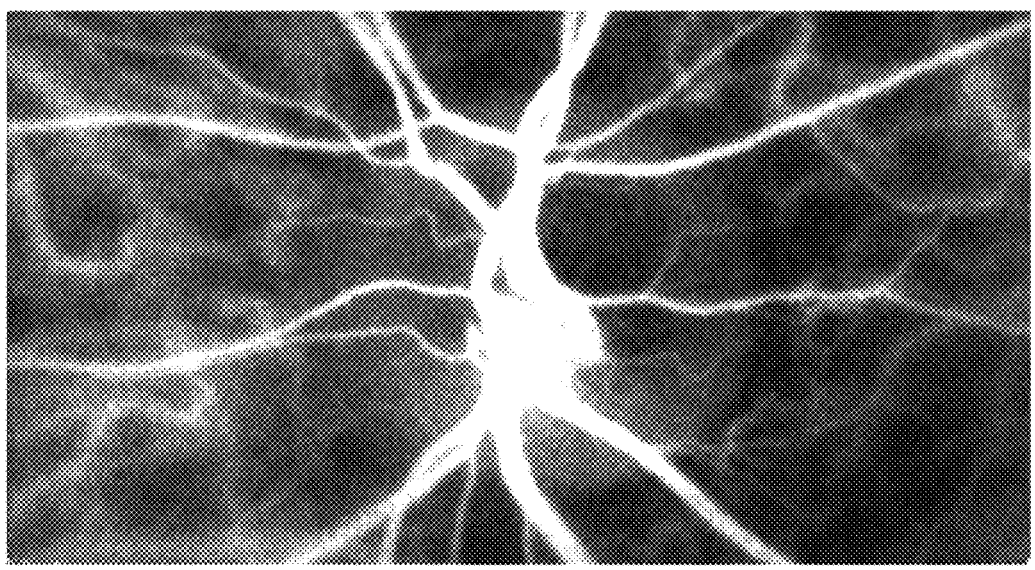
FIG. 4 is an image showing a synthesized blood flow map obtained by capturing eyeground blood flow maps as shown in FIG. 3 (120 frames) and superimposing them while correcting shifts of the eyeground blood flow maps due to eye movement during fixation (an example for the case where the subject is the yellow race).

The noise components originally contained in each blood flow map are averaged by the tracking processing. This allows the contours of blood vessels to be clearly recognized as shown in FIG. 4. FIG. 4 is an image showing a synthesized blood flow map obtained by capturing blood flow maps as shown in FIG. 3 (120 frames) and superimposing them while correcting the shifts of the blood flow maps due to eye movement during fixation (an example for the case where the subject is the yellow race). In general, such a blood flow map is displayed in color code. However, here, the blood flow map is displayed in gray scale, and the higher the degree of whiteness, the greater the blood flow.

Figure 5:
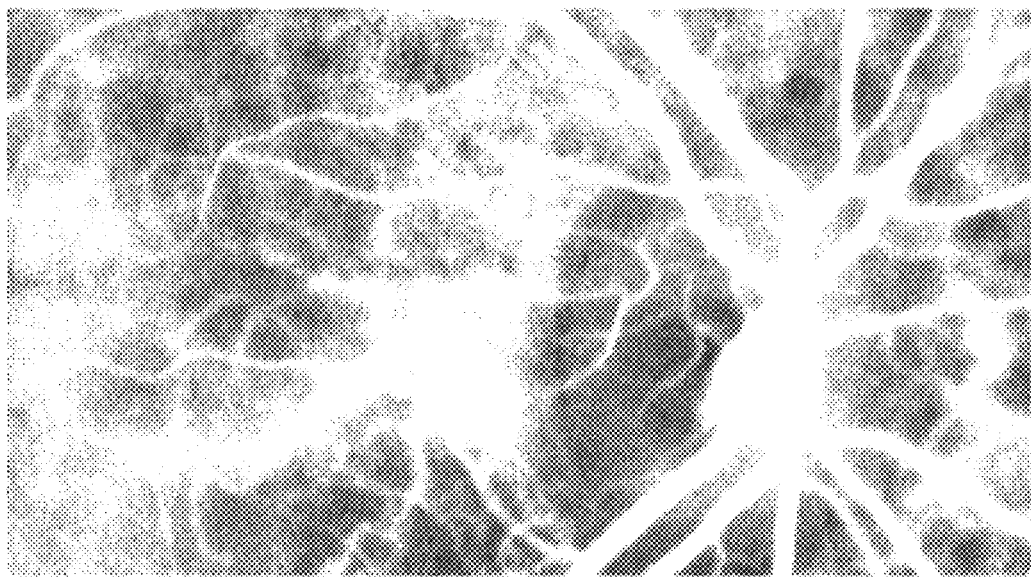
FIG. 5 is an image showing a synthesized blood flow map which is similar to that shown in FIG. 4 but was obtained from a subject of the white race.

Meanwhile, the eyeground blood flow of a caucasoid person is measured using a conventional blood flow image diagnosing device, a synthesized blood flow map of FIG. 5 is obtained. Although the synthesized blood flow map of FIG. 5 is similar to that of FIG. 4, it shows an example of measurement values obtained from people of the white race. FIGS. 4 and 5 correspond to "depiction of a conventional blood flow map" described in FIG. 2. When FIGS. 4 and 5 are compared, it is found that the numerical value is displayed to be considerably high. Under the assumption that the size of the eyeball does not differ greatly among the races, it is considered that the amount of blood circulating within the eyeball does not differ greatly among the races. Therefore, it is inconvenient that different blood flow values are displayed even when the difference is the race only, and some correction is needed. This correction is performed in steps S4 through S8 as described below. A specific procedure of the correction will be described for an example case where the eyeground blood flows of a caucasoid person and a colored person are measured.

Figure 6:
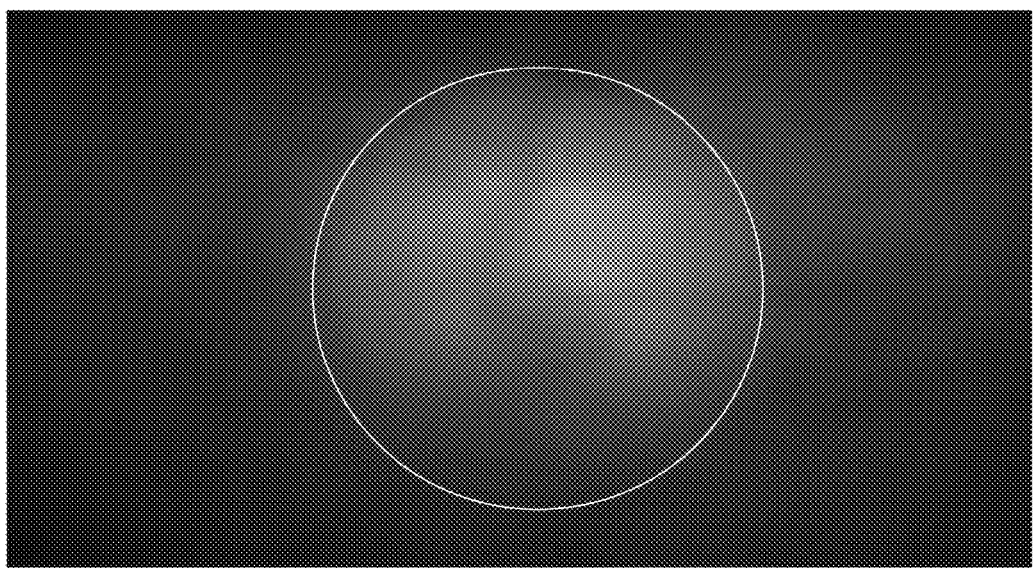
FIG. 6 is an image showing a laser reflection intensity map which is obtained by superimposing speckle images from which the synthesized blood flow map of FIG. 4 is obtained (an example for the case where the subject is the yellow race).
Figure 7:
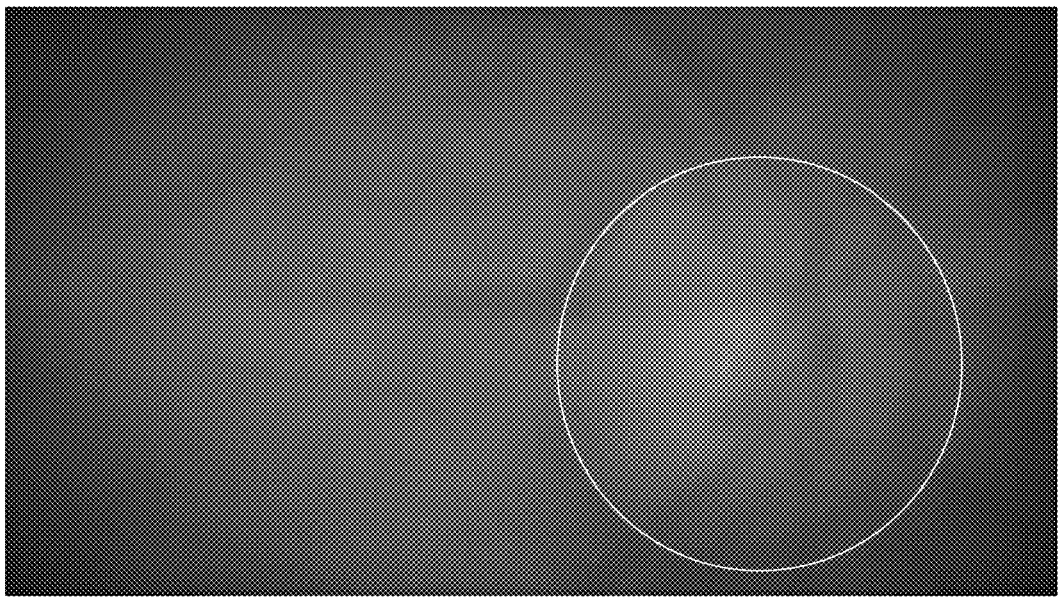
FIG. 7 is an image showing a laser reflection intensity map which is similar to that shown in FIG. 6 but was obtained from a subject of the white race.

In step S4 of FIG. 2, a laser reflection intensity map is synthesized. FIG. 6 is an image showing a laser reflection intensity map which is obtained by superimposing speckle images from which the synthesized blood flow map of FIG. 4 is obtained (an example for the case where the subject is the yellow race). FIG. 7 is an image showing a laser reflection intensity map obtained from a subject of the white race. Information representing the shift of each blood flow map is obtained from the step S3 as tracking information, and tracking is performed on speckle images, on the basis of which the synthesized blood flow map is calculated, in order to average them, a laser reflection intensity map as shown in FIG. 6 is obtained. FIG. 6 shows an example in which the subject is the yellow race. From FIG. 6, it is found that the reflection intensity is high at an optic papilla surrounded by a circle and is low at the remaining portion. FIG. 7 shows an example in which the subject is the white race. From FIG. 7, it is found that little difference is present between the reflection intensity at the optic papilla and that at the remaining portion. This shows that the layer of the pigment epithelium widely spreading at the boundary between the retina and the choroid is dark in color in the case of people of the colored races and is almost clear in the case of people of the white races, and that the reflectance (or absorptivity) of laser light differs among the human races.

The incident intensity used for calculation of the laser reflectance (reflection intensity/incident intensity) (step S7 which will be described below) can be obtained as a signal representing the intensity of laser light radiated from the laser light irradiation system. The laser reflection intensity is obtained as the signal intensity of light reflected from each location within the observation region and detected by the light receiving section. For example, as exemplified above, it can be obtained from the laser reflection intensity map. The power of laser light output from the present blood flow image diagnosing device is adjusted by setting a laser output value using measurement software (step S1). In the case of caucasoid people, the internal scattering is strong, and light returning from the eyeground to the light receiving section is too strong. Therefore, the laser output is decreased. In contrast, in the case of people of the colored races, the light returning to the light receiving section is weak. Therefore, the laser output is set to be rather strong. For example, when the laser output (laser light intensity signal) required to obtain the map of FIG. 6 is considered 10, the laser output required to obtain the map of FIG. 7 is only 5. When the averaged value (reflection intensity) of the laser reflection intensity map in a certain region other than the optic papilla was 60 in the case of colored people, the laser reflectance becomes 6 (=60/10). Similarly, when the averaged value (reflection intensity) of the laser reflection intensity maps in a certain region other than the optic papilla was 80 in the case of caucasoid people, the laser reflectance becomes 16 (=80/5). In other words, the laser reflectance can be determined from the overall output of laser light applied to the eyeball and the average value of the laser reflection intensity map within a region of interest.

In step S5, measurement regions are recognized. For example, the eyeground blood flow is measured mainly in three regions of interest; i.e., the choroid, the retina blood vessel, and the optic papilla tissue. When an eye doctor diagnoses eye diseases, he or she pays attention mainly to the blood flow within blood vessels running on the retina, the tissue blood flow at the optic papilla, and the blood flow of the choroid, which are considered to closely relate to angiostenosis, glaucoma, and macular degeneration caused derivatively by medical diseases such as arteriosclerotic and diabetes. However, since these blood flows differ in the positional relation with the pigment epithelium, they differ in the degree of influence of the pigment concentration. Namely, since the retina blood vessel is located closer to the surface layer than the pigment epithelium layer, when the pigment concentration is high, the backward scattering light from a deeper region decreases, and the reflection intensity of the blood vessel portion also decreases.

In step S6, the measurement regions are classified. Since the pigment concentration and its influence change among the measurement regions, different correction coefficients must be prepared for the respective measurement regions.

In step S7, the laser reflectance of each of the classified regions is calculated. For such calculation, for a large number of healthy persons of all human races (white, yellow, and negroid races), first a blood flow value is obtained from a synthesized blood flow map having undergone tracking processing, and a laser reflectance is obtained from the laser reflection intensity map. The obtained values are stored. The averaged value of the laser reflectance (=reflection intensity/ incident intensity) of each region is obtained using the laser reflection intensity map. The averaged value of the laser reflectance can be considered to reflect the pigment concentration which affects that region. Measurement must be performed a large number of times in order to obtain and store the above-mentioned data. In actual measurement, the stored data are used for correction.

Figure 10:
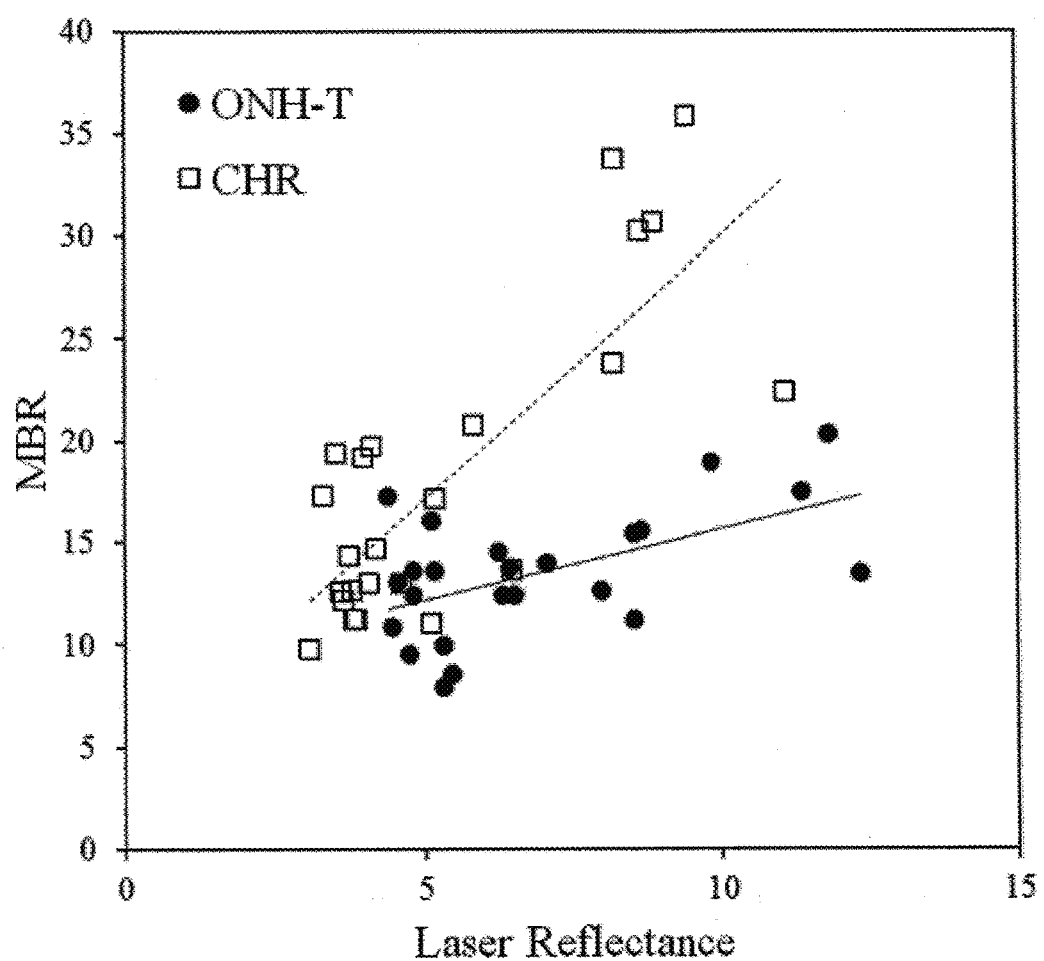
FIG. 10 is a scatter diagram obtained by obtaining the averages of MBR values for two regions (choroid and optic papilla tissue) and plotting them for corresponding laser reflectances, and regression lines.

In step S8, a newly measured blood flow map is corrected. Namely, correction coefficients are applied to the blood flow map in accordance with the laser reflectances of the respective regions. For each region, the averaged laser reflection intensity and the averaged blood flow value are calculated. This calculation is repeated for all the stored data of healthy persons, whereby scatter diagrams are plotted, and regression lines are obtained. FIG. 10 shows scatter diagrams and regression lines obtained for two regions (choroid CHR and optic papilla tissue ONH-T). Each of the scatter diagrams represents the relation between the averaged blood flow value MBR and the laser reflection intensity. Although the inclination of the regression line changes among the regions, for increase and decrease of the laser reflectance in each region, it functions as a correction coefficient. In the example of FIG. 10, data at the right end of the graph are those of the white race, data of the colored races are shown on the left side thereof such that the higher the pigment concentration, the closer to the left end. The relation between the averaged blood flow value MBR and the laser reflectance represented by such a regression line is stored in the image storage section.

Next, there will be considered the case where data of a certain colored race are newly obtained, data of, for example, the choroid is obtained, is converted to a value of the white race, and is compared with its standard value. In this case, the laser reflectance of that region is obtained, and is divided by the average laser reflectance of the white race located at the right end of FIG. 10 (the value stored in the storage section), and a resultant value is used as a correction coefficient. The averaged blood flow value MBR is divided by this correction coefficient, whereby a numerical value corrected for the influence of the pigment can be obtained and can be compared with that of the white race.

Figure 11:
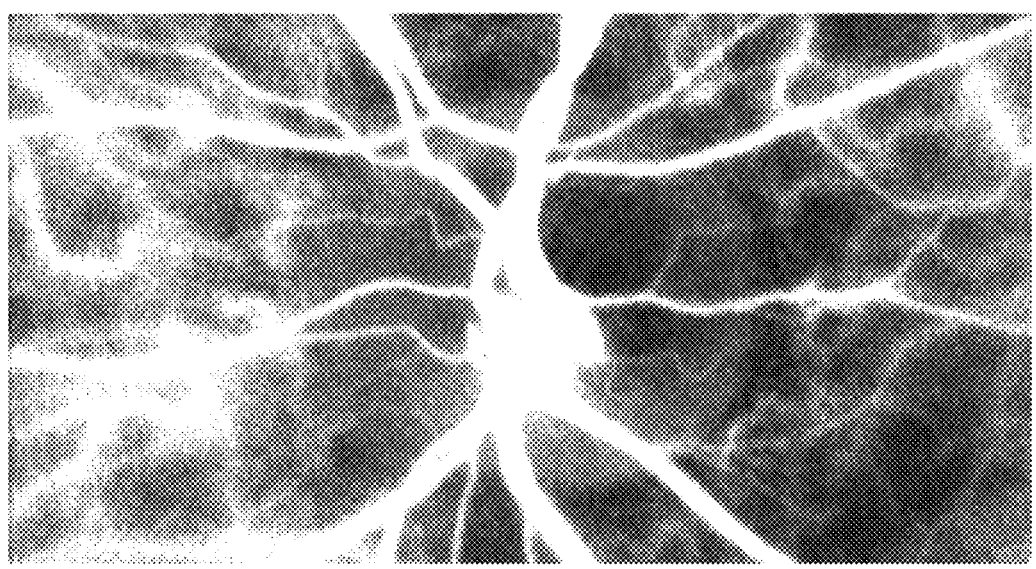
FIG. 11 is an image showing an example of correction in which the correction of the present invention was applied to the blood flow map of FIG. 4 so as to increase the blood flow value of people of the yellow race to a value comparable to that of people of the white race.

In step S9, the corrected blood flow map is depicted. As can be understood from FIG. 10, the correction coefficients of the respective regions differ from one another. However, when the above-described correction is performed for the respective regions, image comparison of the blood flow map becomes possible. FIG. 11 shows the result of correction performed on the blood flow map of the yellow race shown in FIG. 4. FIG. 11 shows that the corrected numeral values are comparable to those of the blood flow map of the white race shown in FIG. 5. Accordingly, even in a country where people of many races live, there can be determined a criteria; e.g., a criteria that when the tissue blood flow of the optic papilla becomes equal to or lower than a predetermined cutoff value, the risk of glaucoma increases irrespective of the human race.

Next, there will be described operation of a second embodiment in which the blood flow image diagnosing device shown in FIGS. 1(A) and 1(B) is applied to measurement of the skin blood flow. Correction similar to that performed for the eyeground blood flow is necessary for the skin blood flow. For example, the concentration of melanin of black people is high, and even near-infrared laser light is easily absorbed. Therefore, the measured value of the subcutaneous blood flow is displayed to be rather low as compared with that of people of the yellow race. It cannot be considered that the flow of blood flowing through the subcutaneous capillary vessel layer formed to nourish the skin tissue differs among the human races. Therefore, it is necessary to introduce a correction method which allows display of standardized numerical values irrespective of the human race. Further, it has been found that the color of the palm of the hand is thin in color as compared with the back of the hand, and the differences among measured values are small as compared with those of the back of the hand. Accordingly, the correction coefficient for the palm of the hand differs from that for the back of the hand, and it is necessary to apply correction on a region-by-region basis as in the case of the eyeground.

A possible method which realizes this is measuring the pigment concentration of a skin tissue of a subject (object under measurement) by using a skin color measurement device or the like and performing correction. However, this investigates the reflecting characteristic (or absorbing characteristic) for visible light, and does not show the characteristic for a laser wavelength used for measurement. Accordingly, the most feasible method is directly obtaining, from a laser scattering signal used for blood flow measurement, information of the characteristic of reflection (or the characteristic of absorption) by the pigment of the subject for the wavelength of the laser signal as in the case of the eyeground.

In the case of the eyeground, the information of the pigment concentration is contained in the laser reflection intensity map shown in FIG. 6 or FIG. 7. A value obtained by dividing the numerical value on this map by the incident intensity of laser light projected to the eyeground shows the ratio of reflection by the pigment (reflectance), which is inverse proportional to absorption. This allows application of first-stage correction. However, as described above, the influence of absorption by the pigment changes depending on the positional relation between a blood vessel or blood vessel layer to be detected and the pigment layer. Therefore, it become necessary to perform second-stage correction. In the second-stage correction, the positional relations are classified into several groups, regions having the same positional relation are recognized as the same region, and a different correction coefficient corresponding to the region is applied.

Although the eyeground blood flow changes slightly within a day, the blood flows at an approximately constant rate all times. In contrast, it is known that the skin blood flow is greatly affected by room temperature, clothing, and metal condition, and, in particular, its change increases toward the distal ends of the extremities. When a concept such as skin perfusion index (SPI) which is a standardized index in which the influence of melanin concentration is cancelled is introduced, it is necessary to first find a reference region which facilitate comparison between individuals or between human races. According to the results of a search conducted by us, the value of the skin of the chest or back whose vibration due to the heartbeat or breathing is small and which is covered with clothes is relatively stable. First, for these portions, the first-stage correction for melanin concentration is performed using the above-described laser reflection intensity map. Next, the second-stage correction is performed. In the second-stage correction, the value corrected through the first-stage correction is multiplied by the correction coefficients of regions (e.g., the palm and back of the hand) which differ in terms of pigment concentration and the scattering characteristic of the corneal layer of epidermis. As described above, in the case of the eyeground and in the case of the skin, by performing correction in the same procedure, it becomes possible to display blood flow maps using a standardized index which allows comparison of blood flow values between people of different races.

EXAMPLES

The index MBR (Mean Blur Rate) that the present inventor uses for calculation of the blood flow value is defined by MBR=(contrast of speckles)$^{-2}$=(average light intensity/standard deviation of fluctuation component)$^2$. In the case of people of the colored race, the MBR value of the retina blood vessel is displayed to be lower, as compared with people of the white race, because of the following reason. The time course change of speckles caused by the blood flow component of a blood vessel portion of people of the colored races is the same as that of people of the white race. However, backward scattering light becomes weak due to the pigment component contained in the background tissue, and the average light intensity (the numerator of the above-described expression) decreases as compared with caucasoid people. As a result, the blood flow value (MBR value) is displayed to be rather low.

Figure 8:
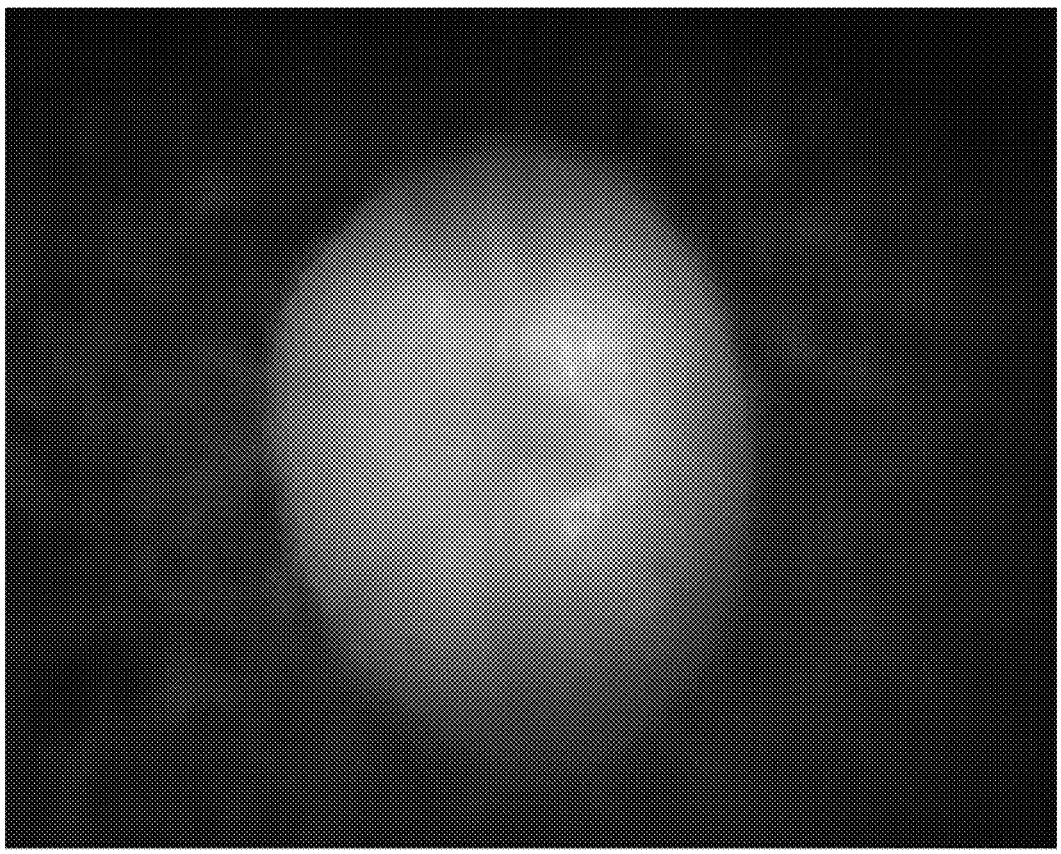
FIG. 8 is an image showing a laser reflection intensity map obtained when a monkey was used as a subject.
Figure 9:
FIG. 9 is an image showing a synthesized blood flow map obtained when a monkey was used as a subject.

In an extreme case, as shown in the laser reflection light distribution of FIG. 8 and the synthesized blood flow map of FIG. 9, the pigment concentration is very high in regions other than the optic papilla. It is considered that no pigment epithelium exists at the optic papilla, and the backward scattering light is strong. Therefore, the blood flow value of the retina blood vessel is displayed to be sufficiently high at the optic papilla; however, when leaving the optic papilla, the blood flow decreases sharply, and it becomes almost impossible to recognize as a blood vessel.

As shown in the examples of FIGS. 4 and 5, in a region around the optic papilla, blood flow maps of the retina blood vessel and the choroid (the blood vessel layer located underneath the retina) are displayed. Although the former is displayed as a thin clear line, the image of the latter becomes blurred because the latter is located on the deeper side and the information is scattered. Further, as is clear from FIG. 5, the choroid blood flow value of people of the white race is displayed to be as high as double that of people of the colored race.

Meanwhile, in the case of people of the colored races as well, no pigment epithelium exists at the optic papilla. Therefore, it was predicted that when the tissue blood flow at the optic papilla is measured, a value similar to that obtained for caucasoid people is obtained. However, when a large number of measurement examples were compared in actuality, it was found that in the case of the caucasoid people, the blood flow value is displayed to be rather high as compared to people of the colored race. Conceivably, this phenomenon occurred for the following reason. In the case of caucasoid people, the degree of light absorption by the pigment epithelium is small. Therefore, laser light repeats multiple scattering within the eyeball, and scattered light reaches the optic papilla. As a result, contrast decreases accordingly, and the MBR value increases slightly.

As described above, the influence of the pigment epithelium on the blood flow index MBR is strongest at the choroid, is second strongest at the retina blood vessel, and weakest at the optic papilla tissue. In other words, this means that when all the values obtained from different regions are multiplied by the same numerical value, proper correction cannot be performed, and that the values obtained from different regions must be multiplied by different correction coefficients determined for the regions.

The important point is that even when a subject thinks that he or she knows his/her race, the actual pigment concentration does not necessarily correspond thereto. Also, it is a common knowledge that, for example, people in Asia have different melanin concentrations state by state or region by region even though they are of the same colored race. A method of creating a database of standard values on a race-by-race basis and performing comparison is widely used in medical equipment. However, in the case where the influencing factor varies among people of the same race, accurate values cannot be obtained unless correction is performed on the basis of some actually measured values of the influencing factor obtained from an object under measurement.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

The invention claimed is:

1. A method of performing blood flow image analysis of a subject using a laser light irradiation system for applying laser light to an observation region of a biotissue having blood cells and a light receiving section having a plurality of pixels and adapted to detect reflection light from the observation region of the biotissue, the method comprising the steps of:

successively capturing a plurality of images on the basis of a signal from the light receiving section, and storing the plurality of images as a plurality of stored images;

computing the speed of blood flow within the biotissue from time course changes of output signals of the plurality of pixels throughout the plurality of stored images, and creating a blood flow map having a two-dimensional distribution using the speed of the blood flow;

obtaining, in advance for a plurality of persons, a relation between laser reflectance and the blood flow value in the observation region of the plurality of persons, and storing the relation, the relation being used for creation of a correction coefficient used for correcting the blood flow map in accordance with the pigment concentration of the observation region;

creating, at the time of new measurement, the correction coefficient on the basis of a newly obtained laser reflectance of the subject and the stored relation between the laser reflectance and the blood flow value, the laser reflectance being obtained from a relation between a laser reflection intensity of the reflection light detected from the observation region, and a signal representing an intensity of laser light radiated from the laser light irradiation system; and correcting the blood flow map in accordance with the created correction coefficient, and therefore displaying the blood flow map corrected on the basis of the correction coefficient by a standardized numerical value irrespective of the race of the subject.

2. A method for diagnosing in a subject a blood flow in an observation region of biotissue having blood cells, the method comprising the steps of:

applying laser light to the observation region of the biotissue;

detecting reflection light from the observation region of the biotissue;

successively capturing a plurality of images from the detected reflection light;

creating a blood flow map for the blood flow within the biotissue from the plurality of captured images, said creating of the blood flow map including providing the blood flow map with blood flow values for the blood flow within the biotissue;

predetermining for a plurality of persons, a population relationship between laser reflectance and blood flow value in an observation region of the plurality of persons;

determining for the subject, a laser reflectance from the observation region of the biotissue of the subject;

creating a correction coefficient based on the laser reflectance from the subject and from the population relationship; and correcting the blood flow values in the blood flow map in accordance with the created correction coefficient;

displaying the blood flow map with the corrected blood flow values.

3. A method in accordance with claim 2, wherein:

said creating of the correction coefficient uses a pigment concentration of the observation region of the subject.

4. A method in accordance with claim 3, further comprising:

determining the pigment concentration from the laser reflectance from the subject, and the laser reflectance is determined from an intensity of the applied laser light and an intensity of the reflection light.

* * * * *